United States Patent
Charlton

(10) Patent No.: US 9,194,837 B2
(45) Date of Patent: Nov. 24, 2015

(54) ANALYTE SENSORS AND SYSTEMS INCLUDING RETENTION TAB AND METHODS OF MANUFACTURING SAME

(75) Inventor: Steven C. Charlton, Osceola, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 442 days.

(21) Appl. No.: 13/589,377

(22) Filed: Aug. 20, 2012

(65) Prior Publication Data

US 2013/0048495 A1 Feb. 28, 2013

Related U.S. Application Data

(60) Provisional application No. 61/527,100, filed on Aug. 24, 2011.

(51) Int. Cl.
*G01N 33/487* (2006.01)
*G01N 27/327* (2006.01)

(52) U.S. Cl.
CPC ........ *G01N 27/3272* (2013.01); *G01N 27/3273* (2013.01); *G01N 33/48757* (2013.01); *G01N 33/48778* (2013.01); *Y10T 29/49826* (2015.01)

(58) Field of Classification Search
CPC .................. A61B 2560/045; A61B 2562/0295; A61B 5/150259; G01N 27/307; G01N 33/49; G01N 27/3272; G01N 27/3273; G01N 33/48757
USPC ........................ 422/68.1, 63, 82.01; 600/365; 204/403.01, 400, 403.02, 406, 407; 205/792; 356/246; 435/14, 287.1, 435/287.7
See application file for complete search history.

(56) References Cited

U.S. PATENT DOCUMENTS

| | | |
|---|---|---|
| 4,721,677 A | 1/1988 | Clark, Jr. |
| 7,364,699 B2 | 4/2008 | Charlton |
| 7,549,323 B2 | 6/2009 | Charlton et al. |
| 7,749,454 B2 | 7/2010 | Charlton |
| 2003/0047451 A1* | 3/2003 | Bhullar et al. ........... 204/403.01 |
| 2006/0127964 A1* | 6/2006 | Ford et al. ........................ 435/14 |
| 2006/0182656 A1 | 8/2006 | Funke et al. |
| 2007/0259431 A1 | 11/2007 | Charlton |
| 2009/0151448 A1 | 6/2009 | Nishina |
| 2010/0241030 A1* | 9/2010 | Fowler et al. ................. 600/583 |
| 2012/0073968 A1 | 3/2012 | Lee et al. |

FOREIGN PATENT DOCUMENTS

WO WO 2011/002152 1/2011

OTHER PUBLICATIONS

International Preliminary Report on Patentability and Written Opinion of International Application No. PCT/US2012/051539 dated Mar. 6, 2014.
International Search Report and Written Opinion of International Application No. PCT/US2012/051539 dated Nov. 6, 2012.

* cited by examiner

*Primary Examiner* — Luan V. Van
*Assistant Examiner* — Gurpreet Kaur
(74) *Attorney, Agent, or Firm* — Dugan & Dugan, PC

(57) ABSTRACT

In some aspects, an analyte sensor is provided for detecting an analyte concentration level in a biological fluid sample. The analyte sensor has a base including a top and bottom side, a lid, and an attachment member including one or more retention tabs coupled proximate the top side so that the analyte sensor can be grasped by the sensor's top side. Manufacturing methods and systems adapted to use and dispense the analyte sensors are provided, as are numerous other aspects.

14 Claims, 14 Drawing Sheets

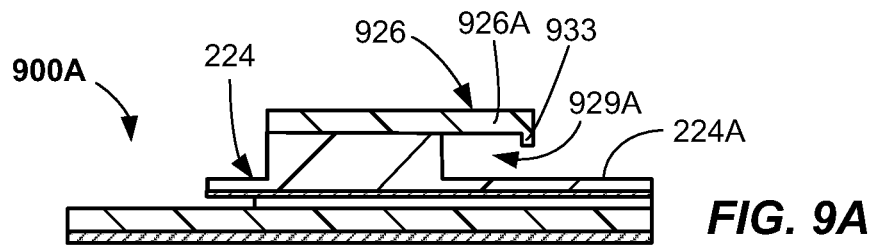
*FIG. 9A*
*FIG. 9B*
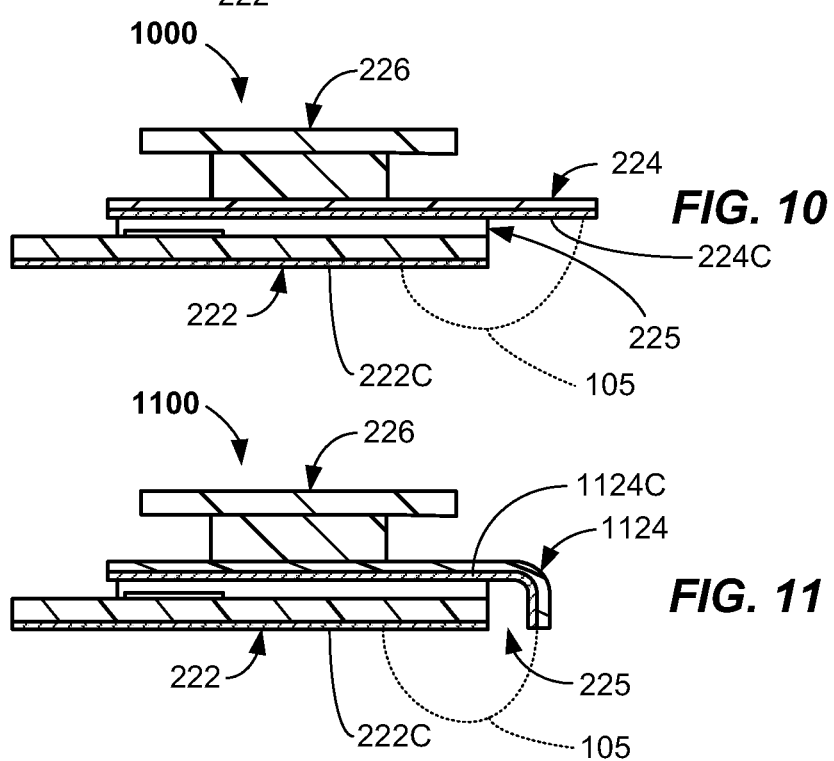
*FIG. 10*
*FIG. 11*

ANALYTE SENSORS AND SYSTEMS INCLUDING RETENTION TAB AND METHODS OF MANUFACTURING SAME

RELATED APPLICATIONS

The present application claims priority to U.S. Provisional Patent Application No. 61/527,100 filed Aug. 24, 2011, and entitled "ANALYTE SENSORS AND SYSTEMS INCLUDING RETENTION TAB AND METHODS OF MANUFACTURING SAME", which is hereby incorporated herein by reference in its entirety for all purposes.

FIELD

The present invention relates to analyte sensors used to detect an analyte concentration level in a biological fluid sample, systems including the analyte sensors, and methods of manufacturing thereof.

BACKGROUND

The monitoring of analyte concentration levels in a biological fluid can be an important part of health diagnostics. For example, an analyte sensor (sometimes referred to as a "test strip") can be employed for monitoring of a patient's blood glucose level as part of diabetes treatment and care. Furthermore, analyte sensors can be used to measure other analytes, such as lactate, keytones, total cholesterol, uric acid, lipids, triglycerides, high density lipoprotein (HDL), low density lipoprotein (LDL), hemoglobin A1c, and the like.

An analyte sensor is used to detect an analyte concentration level in a biological fluid sample such as from a single sample of blood or other interstitial fluid. For example, the biological fluid can be obtained from the patient via a lancet (e.g., by a pinprick or needle). Typically, after a biological fluid sample has been obtained from the patient, such as by the use of a lancet, the biological fluid sample is then transferred to the analyte sensor for measurement of the biological fluid sample's analyte concentration level.

Many conventional analyte sensors are quite large in size and must be handled by the user. However, for ease of use, it is desirable that sensor handling be minimized. Furthermore, it is desirable to reduce the size of such analyte sensor as material cost to produce the analyte sensor can be reduced. However, as analyte sensors are made smaller, handling the analyte sensor becomes more difficult. Moreover, when made smaller, packaging and dispensing the analyte sensor becomes more difficult. Accordingly, there is a need for miniature analyte sensors that are relatively easy to dispense, require little or no handling, and can be packaged in a relatively small volume.

SUMMARY

In a first aspect, an analyte sensor is provided. The analyte sensor includes a base including a top side and bottom side, a lid positioned proximate to the base on the top side, an attachment member positioned proximate to the top side, the attachment member including one or more retention tabs, a fluid-receiving channel having an opening adapted to receive a biological fluid sample, and a chemically-active region provided in the fluid-receiving channel.

In another aspect, an analyte testing system is provided. The analyte testing system includes an analyte meter including a pylon having grasping tabs, and an analyte sensor including a base with a top side, a lid proximate to the base on the top side, and an attachment member proximate to the top side, the attachment member including one or more retention tab engaging with the grasping tabs to secure the analyte sensor to the pylon.

In yet another aspect, an analyte sensor dispenser apparatus is provided. The analyte sensor dispenser apparatus includes a dispenser body having a recess extending in the dispenser body and an opening, and a plurality of analyte sensors provided in a stacked configuration within the recess, the plurality of analyte sensors including an attachment member having one or more retention tabs disposed towards the opening and adapted to be grasped by an analyte meter.

In a method aspect, a method of manufacturing an analyte sensor is provided. The method includes providing a base having a top side, providing a lid having a top side and a bottom side, at least the bottom side of the lid and the top side of the base forming a fluid-receiving channel, providing a chemically-active region in the fluid-receiving channel, and providing an attachment member including one or more retention tabs.

Other features and aspects of the present invention will become more fully apparent from the following detailed description, the appended claims and the accompanying drawings.

BRIEF DESCRIPTION OF THE DRAWINGS

FIGS. 6 through 11 are cross-sectioned side views of alternative embodiments of analyte sensors.

DETAILED DESCRIPTION

Figure 1:
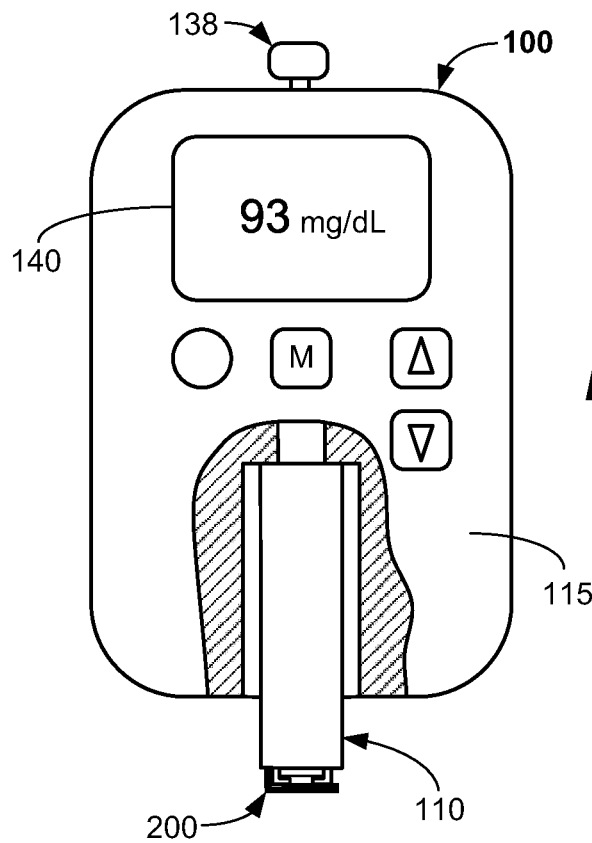
FIG. 1 is a partially cross-sectioned top view of an embodiment of an analyte meter having an embodiment of an analyte sensor coupled thereto.

According to some aspects of the present invention, an analyte sensor that includes an attachment member on a top side is provided. Accordingly, the sensor is readily graspable of a top side thereof. The analyte sensor is configured so that it may be dispensed in a stacked orientation within an analyte sensor dispensing apparatus. The analyte sensor is relatively small in size, and, thus, can be stacked, one atop of each other, in a compact configuration. Because of the small size, material costs in manufacturing the analyte sensor are also minimized. Moreover, the design of the analyte sensor is adapted for mass production. Additionally, blood may dry around the electrical contacts in prior designs making them "sticky," possibly inhibiting electrical contact and possibly biasing the measured result. This possible performance degradation could continue indefinitely. Thus, in one advantage, blood is applied to a bottom side of the sensor (on a side away from the meter) thereby effectively shielding the meter (and electrical connectors or optical read head) from contamination. Further, in one aspect, the sensor design may allow only one sensor to be provided from a dispenser to the meter, possibly reducing user frustration. Positive engagement of a grasping member and grasping tab may provide reliable sensor attachment. Moreover, the sensor design ensures that only the top-most sensor from a dispenser can be captured.

Thus, according to embodiments, the analyte sensor includes an attachment member on a top side thereof. The attachment member includes one or more retention tabs that are adapted to be engaged by grasping tabs of a grasping member. In some embodiments, the grasping member is formed on a pylon of an analyte meter. According to further embodiments, the grasping member is provided at a location proximate to an end of the pylon of the analyte meter, wherein the pylon is adapted to be received in an opening of an analyte sensor dispensing apparatus having the inventive analyte sensors stacked therein. In this manner a single, miniature analyte sensor is attached to the analyte meter by grasping the one or more retention tabs without a user needing to handle the analyte sensor.

In other embodiments, an analyte sensor dispenser apparatus is provided. The analyte sensor dispenser apparatus includes a dispenser body having a recess extending in the dispenser body and an opening. A plurality of analyte sensors are provided in a stacked configuration within the recess. Each analyte sensor includes an attachment member including one or more retention tabs disposed towards the opening, the attachment member being adapted to be grasped by a grasping member of an analyte meter.

In an electro-chemical embodiment, the analyte sensor includes electrical conductors and electrical contact pads that are adapted to make electrical contact with electrical connectors located proximate to an end of a pylon of the analyte meter. The electrical contact pads and conductors are located on a same side of a base as the attachment member, i.e., on the top side. Optical analyte sensor embodiments are also disclosed.

These and other embodiments of analyte sensors, systems including the analyte sensors and methods for manufacturing the analyte sensors are described below with reference to FIGS. 1-17L.

Figure 12A:
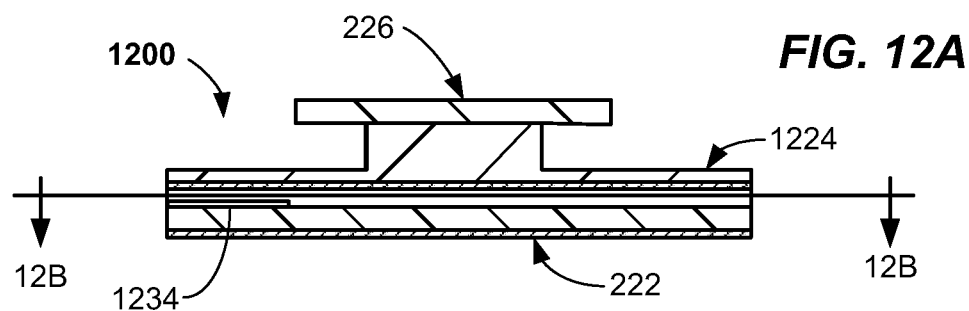
FIGS. 12A and 12B are cross-sectioned side and top views of an alternative embodiment of an optical analyte sensor.
Figure 12B:
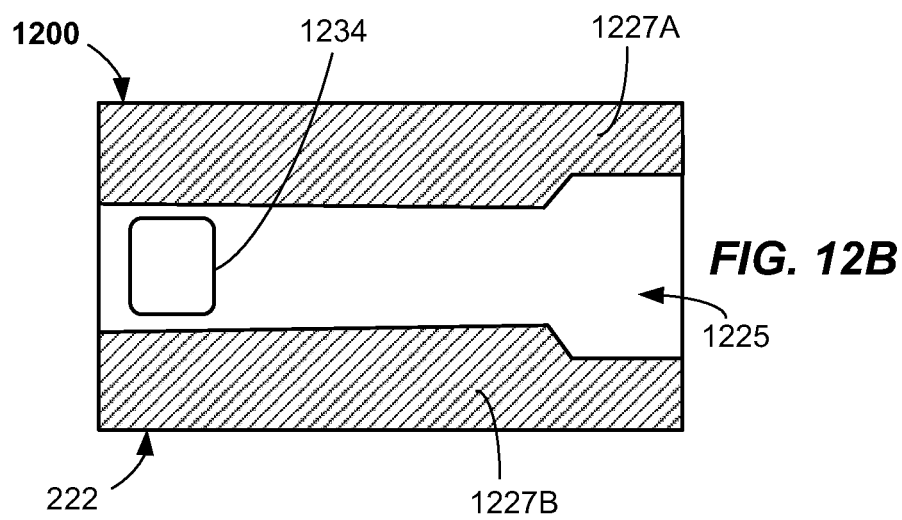
Figure 14:
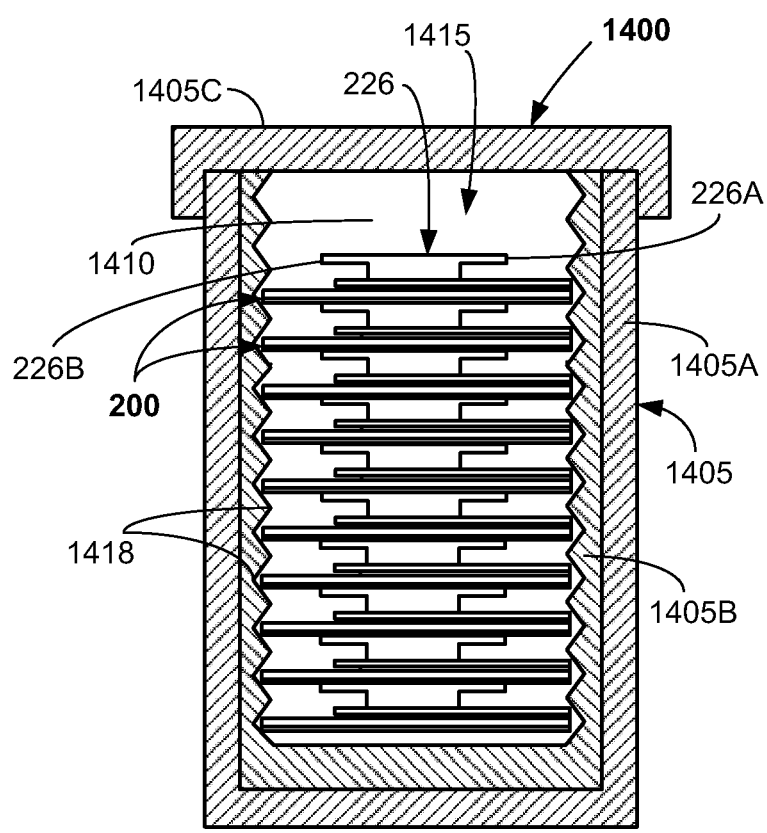
FIG. 14 is a cross-sectioned side view of an example embodiment of an analyte sensor dispenser apparatus adapted to dispense analyte sensors including an attachment member with one or more retention tabs.

FIG. 1 illustrates a top view of a first example embodiment of an analyte meter 100 and attached analyte sensor 200. The analyte meter 100 in the depicted embodiment includes a pylon 110 adapted to receive and configured to couple with and secure the analyte sensor 200 by a top side thereof. The pylon 110 extends from a body 115 of the analyte meter 100 and is adapted to be received in an opening of an analyte sensor dispenser apparatus (FIG. 14). The analyte sensor 200 in the described embodiment is an electrochemical analyte sensor. However, it should be apparent based upon the following description that the invention is equally applicable to analyte sensors functioning based upon a color change, i.e., optical analyte sensors as are depicted in FIGS. 12A-12B.

Figure 2A:
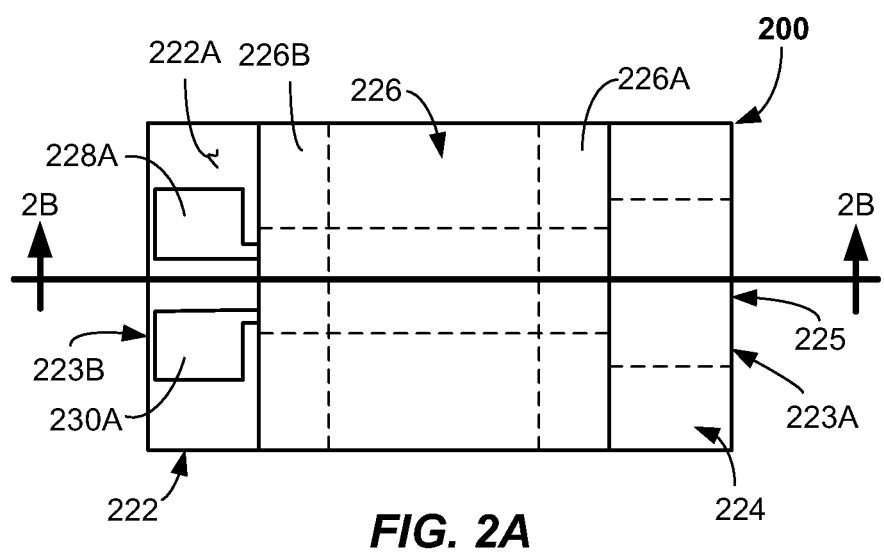
FIG. 2A is an enlarged top plan view of an embodiment of an analyte sensor.
Figure 2B:
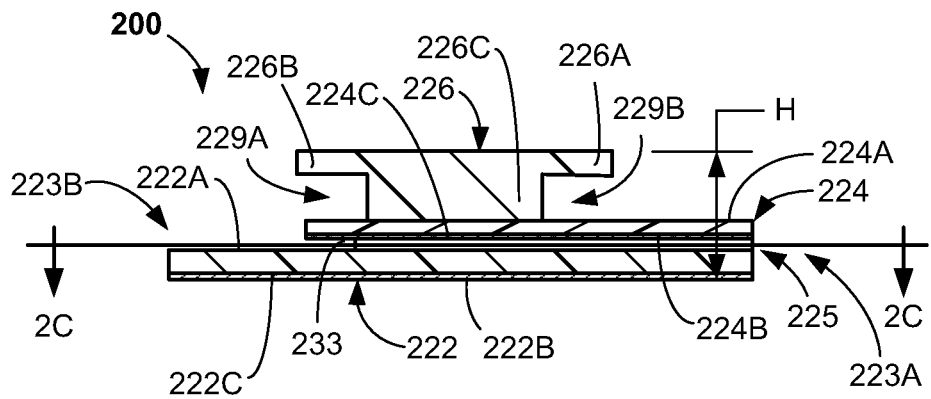
FIG. 2B is a cross-sectioned side view of an embodiment of analyte sensor of FIG. 2A taken along section line 2B-2B.
Figure 2C:
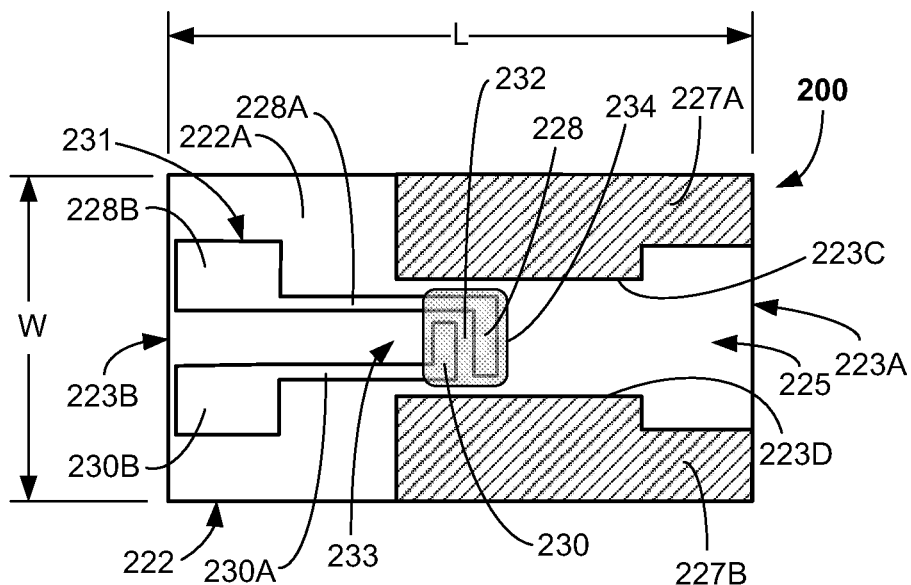
FIG. 2C is a cross-sectioned top view of an embodiment of analyte sensor of FIG. 2B taken along section line 2C-2C.

Now referring to the embodiment depicted in FIGS. 2A-2C, the analyte sensor 200 includes a base 222 preferably formed of an insulating material. The base 222 can be manufactured from a polymer material, such as a polycarbonate, polyethylene terephthalate, polyimide, high density polyethylene, or polystyrene material, for example. Other materials can be used. The base 222 can be stamped out or thermally formed or molded. In some embodiments, the base 222 is a sheet of material having coplanar sides. In the embodiment shown, the analyte sensor 200 has a first end 223A adapted to receive a biological fluid sample and a second end 223B opposite the first end 223A adapted to make electrical connection to the analyte meter 100 (FIG. 1). The base 222 includes a top side 222A and bottom side 222B. Top side and bottom side are used herein for illustration purposes, and are not meant to require any particular orientation when in use. In some embodiments, the base 222 includes an optional hydrophobic layer 222C applied on the bottom side 222B thereof. Hydrophobic layer 222C can be a layer of silicone material of about 0.005 mm thick, for example. Other types of hydrophobic materials can be used. The function of the hydrophobic layer 222C is to repel and direct the biological fluid sample (e.g., blood) to a fluid-receiving channel 225 at the first end 223A and minimize unused biological fluid sample clinging to the base 222.

In the depicted embodiment, the analyte sensor 200 further includes a lid 224 positioned proximate to the base 222 on the top side 222A. As shown, at least the lid 224 and top side 222A of the base 222 cooperate to form a fluid-receiving channel 225 having an opening adapted to receive a biological fluid sample therein. The lid 224 includes a top side 224A and a bottom side 224B and can include an optional hydrophilic coating 224C on the bottom side 224B to facilitate fluid sample flow into the fluid-receiving channel 225. This hydrophilic coating 224C can be a layer of dioctyl sodium sulfosuccinate material of about 0.01 mm thick, for example. Other hydrophilic materials can be used.

In the embodiment shown, the fluid-receiving channel 225 extends along an axial length of the analyte sensor 200 and terminates a distance away from the first end 223A. The lid 224 is suitably directly or indirectly coupled to the base 222. For example, the lid 224 can be adhered, fused, or mechanically fastened to the base 222 by an adhesive and/or heat and pressure and/or interfering members (e.g., a snap fit). In some embodiments, the lid 224 is a planar member with top and bottom sides being coplanar. In some embodiments, one or more suitable spacers 227A, 227B are provided between the base 222 and lid 224 and function to space the lid 224 from the top side 222A of the base 222 by a desired distance to form the fluid-receiving channel 225, and to couple the lid 224 to the base 222. In other embodiments, the channel is molded into the lid 222 or base 224.

In the depicted embodiment, the spacers 227A, 227B are made of coplanar sheet material. Other configurations can be used. Spacers 227A, 227B and lid 224 can be made from a same or similar material as the base 222 and/or lid 224, for example. Dissimilar materials can be used as well. The base 222, lid 224, and spacers 227A, 227B can be adhered together by any suitable means, such as by the use of an adhesive, heat and/or pressure, or mechanical fastening. As will be apparent from the method of manufacturing described below, multiple ones of the base 222, lid 224, and spacers 227A, 227B can be formed on individual sheets of material.

As shown in FIGS. 2B-2C, the analyte sensor 200 can have a length (L) of between about 5 mm and 15 mm, and in some embodiments about 6.5 mm. The analyte sensor 200 can have a width (W) of between about 3 mm and 10 mm, and in some embodiments about 4.5 mm. The analyte sensor 200 can have a height (H) of between about 1 mm and 3.5 mm, and in some embodiments about 1.7 mm. Other dimensions can be used.

Again referring to FIGS. 2A-2B, according to embodiments of the analyte sensor 200, an attachment member 226 is provided on a top side of the analyte sensor 200 that is proximate to the top side 222A, i.e., on the same side as the top side, to facilitate attachment to and securing of the analyte sensor 200 to the analyte meter 100 (FIG. 1). The attachment member 226 can be formed as a separate member or an integral part of the lid 224. In some embodiments, the attachment member 226 is a separate member coupled to the lid 224 by an adhesive or mechanical fastening, for example. The attachment member 226 includes one or more retention tabs. For example, the depicted embodiment includes two retention tabs 226A, 226B. As shown, the retention tabs 226A, 226B extend along the top side of the lid 224 in generally opposite directions. In some embodiments, the first retention tab 226A extends in a first direction parallel to a surface of a top side of the lid 224 and the second retention tab 226B extends in a second direction parallel to the surface of the top side of the lid 224, but in a direction opposite to the first direction. In the depicted embodiment, the retention tabs 226A, 226B are spaced from a plane of the base 222.

Furthermore, in the depicted embodiment, the attachment member 226 includes a tab spacer 226C. The tab spacer 226C functions to space the retention tabs 226A, 226B away from the top side 224A of the lid 224 and form one or more grasping recesses 229A, 229B between the lid 224 and the one or more retention tabs 226A, 226B. The one or more retention tabs 226A, 226B are adapted to be grasped by a grasping member 336. For example, the one or more retention tabs 226A, 226B at least partially form the one or more grasping recesses 229A, 229B and receive grasping tabs 336A, 336B (FIG. 3A) formed on a pylon 110 of an analyte meter 100 to secure the analyte sensor 200 to the pylon 110.

In the depicted embodiments, the lid 224 comprises a planar top side portion and the attachment member 226 extends away from the planar top side portion in a direction normal to the top side 222A of the base 222. Accordingly, in the depicted embodiments, the top side 224A of the lid 224 defines a first plane and the bottom surfaces of the retention tabs 226A, 226B define a second plane that is spaced from the first plane, wherein the grasping recesses 229A, 229B are formed in between. In any event, the retention tabs 226A, 226B are spaced from the top surface of the lid 224 in a direction normal to the plane of the base 222.

The attachment member 226 can be manufactured from a suitable material, such as polyethylene terephthalate, polycarbonate, or polystyrene, and can be cut from a molded sheet, or formed from several sheets, for example. Optionally, the attachment member 226 may be formed by extrusion. Other materials and manufacturing methods can be used. The length, width, and thickness of the one or more retention tabs 226A, 226B should be sized so that the analyte sensor 200 can be coupled to and secured by the grasping member 336 of the analyte meter 100.

Figure 4:
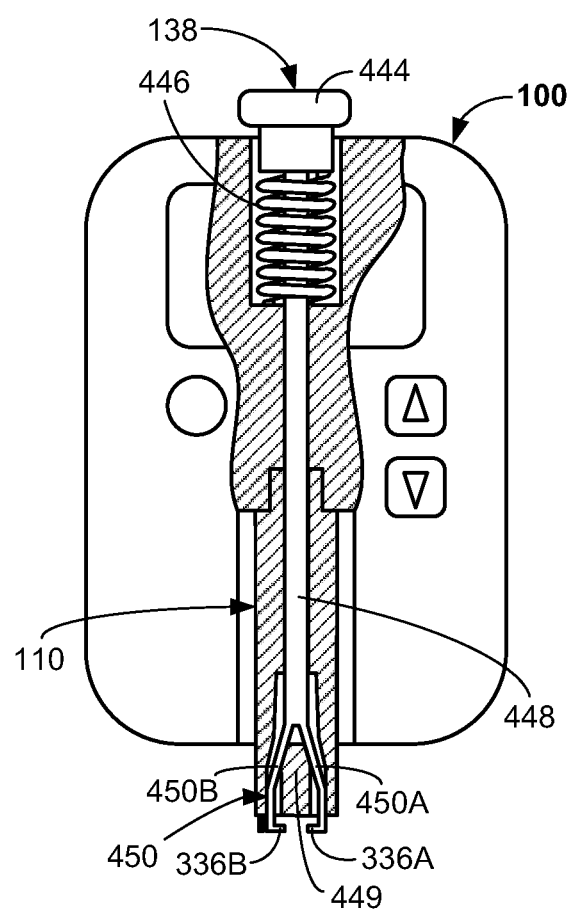
FIG. 4 is a partially cross-sectioned top view of an analyte meter illustrating an example embodiment of a retraction mechanism adapted to retract grasping tabs and release an analyte sensor.
Figure 5:
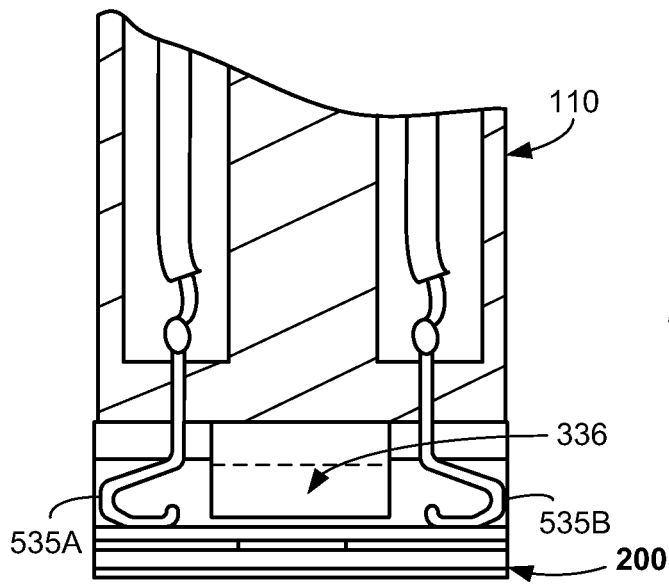
FIG. 5 is a partial cross-sectioned side view of an alternative embodiment of electrical connector adapted to contact the electrical contact pads of the analyte sensor.
Figure 6:
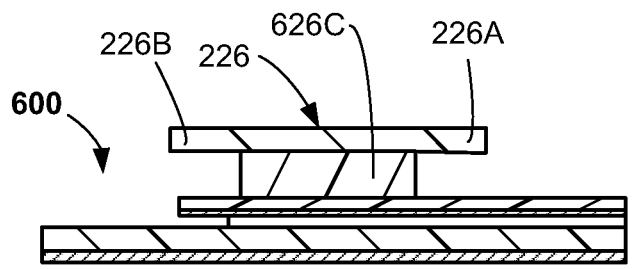
Figure 7:
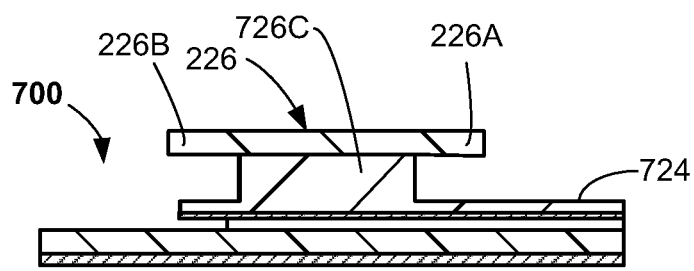
Figure 8:
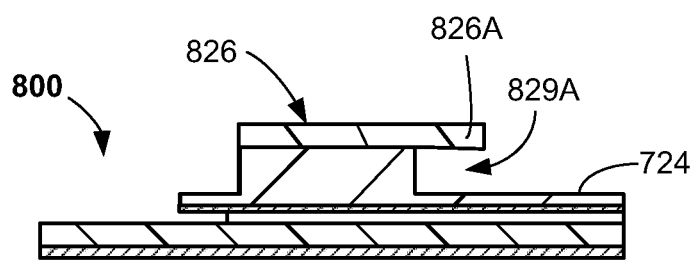

As will be apparent, in some embodiments one or both of the grasping tabs 336A, 336B of the grasping member 336 can be moveable. The ability to move (e.g., laterally) allows for a controlled release of the attachment member 226, such that the analyte sensor 200 can be released from the pylon 110 (e.g., for disposal thereof after use). To accomplish motion of one or both of the grasping tabs 336A, 336B, the grasping member 336 can be operationally coupled to a user-operable mechanism 138 as shown in FIG. 1 and FIG. 4. The user-operable mechanism 138 is adapted to initiate movement of the grasping tabs 336A, 336B to release the analyte sensor 200 from the pylon 110. In other embodiments, the grasping tabs 336A, 336B are fixed to the end of the pylon 110 but are sufficiently flexible so that they can flex and snap over the one or more retention tabs 226A, 226B upon being pushed onto the analyte sensor 200.

Figure 3A:
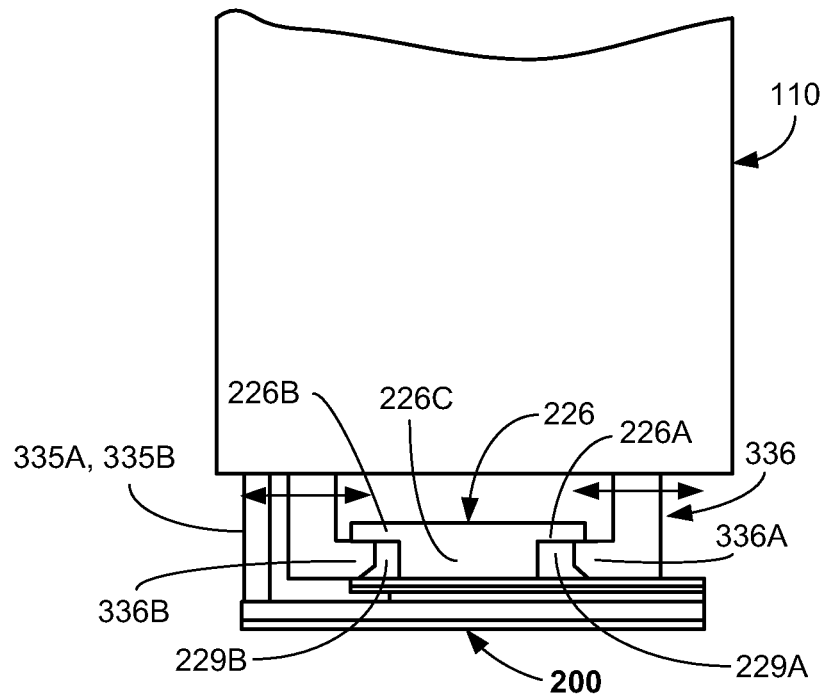
FIG. 3A is a partial side plan view of an embodiment of analyte sensor coupled to a pylon (only a portion shown) of an analyte meter.

FIG. 4 illustrates an example of an analyte meter 100 including a user-operable mechanism 138 adapted to grasp and secure an analyte sensor 200, and then allow the release of the analyte sensor 200 after use/testing via action of a user. In more detail, the user-operable mechanism 138 in the depicted embodiment includes grasping tabs 336A, 336B coupled to any suitable mechanism that allows motion (e.g., an opening and closing movement) of one or more of the grasping tabs 336A, 336B. In the illustrated embodiment, in a closed catch configuration, the grasping tabs 336A, 336B are positioned closer together, and are engaged with and are received into the grasping recesses 229A, 229B (FIG. 3A). In an opened catch configuration, a user depresses a button 444 or other actuating device thereby depressing a spring 446 and actuating a drive rod 448 attached to the button 444. Actuation of the drive rod 448 causes opening of the grasping tabs 336A, 336B. In the depicted example, a cam 449 in the pylon 110 engages the insides of legs 450A, 450B of the catch 450. This spreads the grasping tabs 336A, 336B apart and allows the analyte sensor 200 to be released from the pylon 110. Catch 450 and drive rod 448 can be made of a flexible plastic material, such as a thermoplastic. Other types of suitable mechanisms can be used to move one or more of the grasping tabs 336A, 336B to open and close them relative to one another.

However as described above, in some embodiments, the grasping tabs 336A, 336B are fixed, but flexible. Removal from the pylon 110 in this instance is by the action of the user displacing the analyte sensor sideways by sliding the analyte sensor laterally out of the grasping recesses or by a push button knock out mechanism.

Figure 3B:
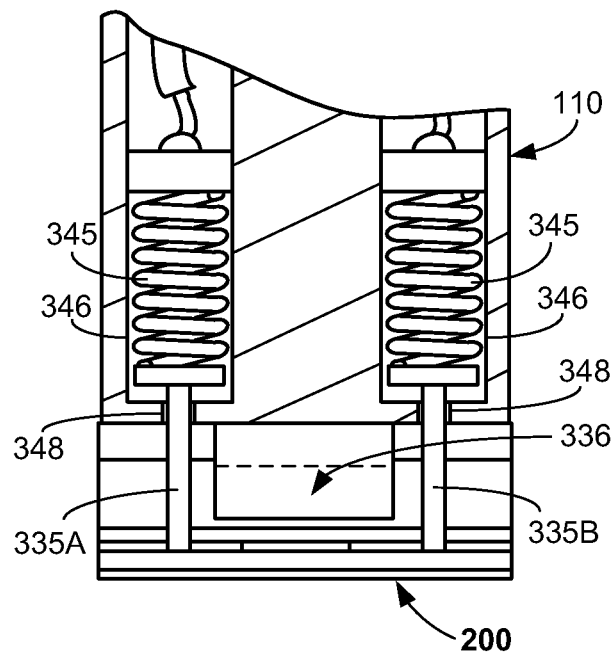
FIG. 3B is a partial cross-sectioned side view of an embodiment of pylon illustrating an electrical connection to electrical contact pads of an analyte sensor.

Now referring to FIG. 3B, in the "as installed" condition, wherein the analyte sensor 200 is being grasped by the grasping member 336, the electrical contact pads 228B, 230B of the analyte sensor 200 are provided in intimate electrical contact with electrical connectors 335A, 335B extending from the pylon 110 of the analyte meter 100 to provide an electrical connection to the analyte meter 100. In the depicted embodiment, the electrical connectors 335A, 335B are moveable or depressible such that electrical contact between the electrical contact pads 228B, 230B is made as the grasping member 336 grasps the analyte sensor 200. The depressible or moveable electrical connectors 335A, 335B can be provided by any suitable spring, such as coil springs 345 received in holes 346 that allow the electrical connectors 335A, 335B to move axially in slides 348 (e.g., guide holes). Suitable connection to the electrical connectors 335A, 335B can be made via soldered wires. Other suitable spring-biased electrical connectors 535A, 535B can be used, such as the leaf spring connectors shown in FIG. 5 secured to the pylon 110. Additional electrical contacts and connectors can be provided, as needed, such as for under fill detection.

Again referring to FIG. 2A-2C, the fluid-receiving channel 225 is adapted to receive a biological fluid sample inserted through an opening thereof, such as at the first end 223A. In particular, the fluid-receiving channel 225 in the depicted embodiment is at least partially formed and defined, for example, by top side 222A of the base 222 and the bottom side 224B of the lid 224, and the inner sides 223C, 223D of the spacers 227A, 227B. The fluid-receiving channel 225 can have any suitable shape (e.g., rectangular), but preferably a shape that promotes capillary action to cause a droplet of biological fluid to be drawn into the fluid-receiving channel 225 when applied at the first end 223A. As the drop of biological fluid sample is applied, the hydrophobic layer 222C aids in ease of movement of the biological fluid sample to the fluid-receiving channel 225 where the biological fluid sample is able to touch the lid 224 and be drawn into the fluid-receiving channel 225. The configuration of the sensor 200 protects the analyte meter 100 from contamination by the biological fluid sample because the biological fluid sample is applied at an end located (e.g., the bottom end 222B) away from the pylon 110 and the electrical contact pads 228B, 230B. In use, the biological fluid sample (e.g., blood) is drawn into the fluid-receiving channel 225 with the assistance of the hydrophilic layer 224C applied on the bottom side 224B of the lid 224, traverses the fluid-receiving channel 225, and comes into intimate contact with a chemically-active region 234 provided in the fluid-receiving channel 225. The fluid-receiving channel 225 can have a length of about 2 mm to 5 mm and a width of about 0.5 mm to 1.5 mm, for example. Other dimensions can be used. One or more vents 233 (FIG. 2A-2C), such as a hole or port, exiting to atmosphere at a point beyond the chemically-active region 234 can be provided to assist in the capillary action.

In the depicted embodiment, a first electrode 228 and a second electrode 230 are provided in the fluid-receiving channel 225. The electrodes 228, 230 are spaced apart and include a gap 232 there between. The chemically-active region 234 is provided in the gap 232. The chemically-active region 234 is provided in contact with the first electrode 228 and second electrode 230 such that there is electrical coupling therewith during use of the analyte sensor 200. The chemically-active region 234 can be applied by any suitable means, such as by spraying over a defined-area mask to control the application area. Such application methods are well known in the art and will not be repeated herein.

A first conductor 228A is provided in electrical contact with the first electrode 228 and extends along the top side 222A of the base 222 and terminates at the first electrical contact pad 228B. Likewise, a second conductor 230A is provided in electrical contact with the second electrode 230 and extends along the top side 222A of the base 222 and terminates at the second electrical contact pad 230B. In the depicted embodiment, the first and second electrical contact pads 228B, 230B are formed on the top side 222A the base 222 and are adapted to be in electrical connection and communication with electrical connectors of an analyte meter 100 (FIG. 3A-3B). Any suitable shape and size of the electrical contact pads can be used.

The first and second electrodes 228, 230, first and second conductors 228A, 230A, and first and second electrical contact pads 228B, 230B make up an electrical circuit pattern 231. The electrical circuit pattern 231 can be made from any suitable electrically-conductive material. Suitable materials include carbon, graphite, gold, silver, palladium, platinum, carbon/graphite polymer thick film (PTF), silver/silver chloride or any suitable electrically-conductive ink such as a carbon and silver-containing ink or combinations. Other conductive materials can be used. The first and second electrodes 228, 230, first and second conductors 228A, 230A, and first and second electrical contact pads 228B, 230B can be applied to or formed on the base 222 by any suitable method, such as by deposition, printing, imaging, plating, film, foil or strip application, or by subdividing a conductive film. In a preferred implementation, the first and second electrodes 228, 230, first and second conductors 228A, 230A, and first and second electrical contact pads 228B, 230B can be formed on the base 222 by subdividing a conductive surface with a laser or other scribing process. Other suitable methods can be used.

As depicted, the first and second conductors 228A, 230A extend through the vent 233 to the first and second electrodes 228, 230. Furthermore, as depicted, the vent 233 is connected to the fluid-receiving channel 225 and has an opening that extends in a direction towards the electrical contact pads 228B, 230B such that direct electrical connection can be made.

The chemically-active region 234 is applied onto portions of the first and second electrodes 228, 130 or otherwise coupled thereto. Briefly, however, the chemically-active region 234 is adapted to be exposed to the biological fluid sample contained in the fluid-receiving channel 225. The chemically-active region 234 is electrochemically active and can include one or more catalytic agents or reagents adapted to promote an electrochemical reaction between an analyte in the biological fluid sample and the catalytic agents or reagents included in the chemically-active region 234, or otherwise generate an electrical current upon being exposed to the biological fluid sample. The mobile electrons produced are conducted to the analyte meter (FIG. 1), for example, through the electrical circuit 231. The electrical connectors of the meter 100 are electrically coupled to processing electronics in the analyte meter 100 to process the received readings and produce analyte data (e.g., analyte concentration readings) that can then be displayed, for example, by the analyte meter 100.

One group of catalytic agents useful for providing the chemically active region 234 are the class of oxidase enzymes which includes, for example, glucose oxidase (which converts glucose), lactate oxidase (which converts lactate), and D-aspartate oxidase (which converts D-aspartate and D-glutamate). In embodiments in which glucose is the analyte of interest, glucose dehydrogenase (GDH) can optionally be used. Pyrolloquinoline quinine (PQQ) or flavin adenine dinucleotide (FAD) dependent enzymes can also be used. A more detailed list of oxidase enzymes that can be employed in the present invention is provided in U.S. Pat. No. 4,721,677, entitled "Implantable Gas-containing Biosensor and Method for Measuring an Analyte such as Glucose" to Clark Jr. which is hereby incorporated by reference herein in its entirety. Catalytic enzymes other than oxidase enzymes can also be used.

The chemically-active region 234 can include one or more layers (not explicitly shown) in which the catalytic agents (e.g., enzymes) and/or other reagents are immobilized, deposited, or printed. The one or more layers can be made of various polymers, for example, including silicone-based or organic polymers such as polyvinylpyrrolidone, polyvinylalcohol, polyethylene oxide, cellulosic polymers such as hydroxyethylcellulose or carboxymethyl cellulose, polyurethanes, block copolymers, sol-gels, etc. A number of different techniques can be used to immobilize the enzymes in the one or more layers in the chemically-active region 234 including, but not limited to, coupling the enzymes to the lattice of a polymer matrix such as a sol-gel, cross-linking the agents to a suitable matrix such as glutaraldehyde, electropolymerization, and formation of an array between the enzymes via covalent binding, or the like.

In some embodiments, a mediator can be included within the chemically-active region 234 to promote the conversion of the analyte to detectable reaction products. Mediators comprise substances that act as intermediaries between the catalytic agent and the electrodes 228, 230. For example, a mediator promotes electron transfer between the reaction center where catalytic breakdown of an analyte takes place and one of the electrodes 228, 230. Suitable mediators include one or more of the following: metal complexes including ferrocene and its derivatives, ferrocyanide, phenothiazine derivatives, phenazine derivatives, osmium complexes, quinines, phthalocyanines, organic dyes as well as other substances. In some embodiments, the mediators are cross-linked along with catalytic agents directly to one or both of the electrode 228, 230.

In operation, after application of a droplet of biological fluid sample at or near the first end 223A of the analyte sensor 200, and subsequent insertion of the droplet of biological fluid sample into the fluid-receiving channel 225 such that it is drawn in and comes into contact with the chemically-active region 234, an electrical current is generated proportional to a concentration of the analyte in the biological fluid sample. In the electrochemical sensor embodiment, a generated electrical current is conducted by the electrical circuit pattern 231, is appropriately conditioned, and is displayed by any suitable readout, such as in a digital readout 140 of an analyte meter 100 (e.g., a blood glucose meter) as shown in FIG. 1. Because the analyte sensor 200 is attached to the end of the pylon 110, and a biological fluid sample is applied near the end 223A, the body and configuration of the analyte sensor 200 also serves to shield the electrical contacts 335A, 335B (FIGS. 3A-3B) from contamination by the biological fluid sample. The same is true of the other embodiments described herein.

As shown in FIGS. 6-10, the analyte sensor can be constructed in a number of optional configurations. For example, in the analyte sensor 600 shown in FIG. 6, the tab spacer 626C can be a separate member from the top portion of the attachment member 226 forming the retention tabs 226A, 226B. In another optional configuration of analyte sensor 700 shown in FIG. 7, the tab spacer 726C comprises a portion of the lid 724 and is formed integrally therewith, such as by molding. In another optional configuration of analyte sensor 800 shown in FIG. 8, the attachment member 826 comprises only a single retention tab 826A and a single grasping recess 829A formed between the retention tab 826A and the lid 724. The single retention tab 826A is adapted to be grasped by a suitable grasping member. Further optional configurations of analyte sensors 900A and 900B are shown in FIGS. 9A-9B. In these embodiments, the attachment member 926 comprises only a single retention tab 926A and a single grasping recess 929A is provided. The single retention tab 926A includes a lip 933 to help the grasping member retain the analyte sensor 900A, 900B, i.e. prevent lateral slippage between the grasping member and the retention tab 926A. In the depicted embodiment of FIG. 9B, the attachment member 926 is shown attached to a top side 222A of the base 222, whereas in the depicted embodiment of FIG. 9A, the attachment member 926 is shown attached to the top side 224A of the lid 224. However, in each embodiment, the attachment member 926 is attached proximate a top side of the base 222. Thus, the analyte sensors 900A, 900B are secured at a top side thereof.

Several additional alternative embodiments of analyte sensors are shown in FIGS. 10-11 that attempt to improve the ability of a droplet of biological fluid 105 applied to the analyte sensor to be drawn into the fluid-receiving channel 225 thereof. FIG. 10 illustrates an alternative embodiment where the lid 224 overlaps the base 222 along the entire width so that a droplet of biological fluid 105 applied (droplet shown dotted) is repelled by the hydrophobic coating 222C of the base 222 and attracted to the hydrophilic coating 224C and readily drawn into the fluid-receiving channel 225.

In the FIG. 11 embodiment, a lid 1124 of the sensor 1100 is bent over along the width of one end so that a droplet of biological fluid 105 applied (droplet shown dotted) is repelled by the hydrophobic coating 222C of the base 222 and attracted to the hydrophilic coating 1124C of the lid 1124 and readily drawn into the fluid-receiving channel 225. Accordingly, an entry into the fluid-receiving channel 225 is disposed on the underside of the base 222.

In the optical color change embodiment shown in FIG. 12A-12B, the body of the optical analyte sensor 1200 is structured and configured in a similar manner as in the previously-described electrochemical embodiments. However, in this embodiment, the chemically-active region 1234 undergoes a chromatic color change when exposed to the biological fluid sample in the fluid-receiving channel 1225.

Figure 13:
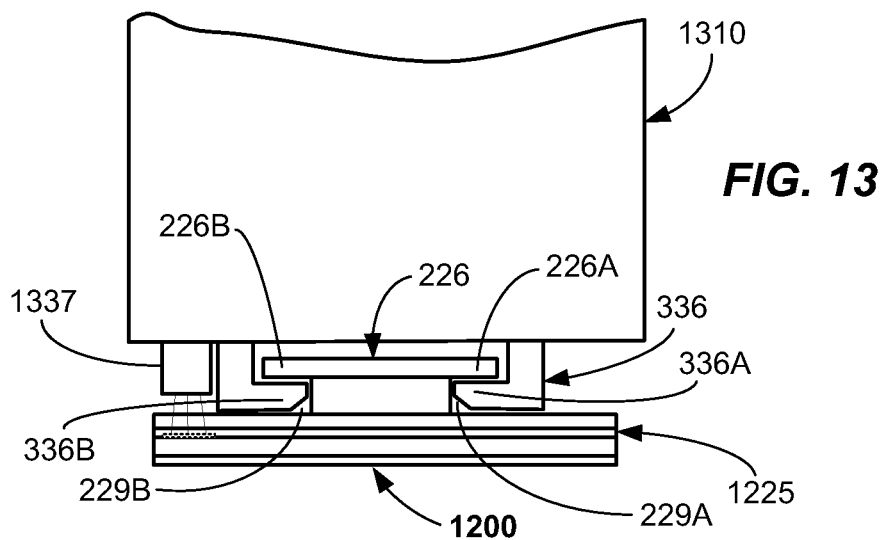
FIG. 13 is a partial side plan view of an embodiment of optical analyte sensor coupled to a pylon (only a portion shown) of an analyte meter.

As shown in FIG. 13, the color change is picked up by an optical read head 1337 through the lid 1224 manufactured from a transparent material (e.g., acrylic or polyester plastic), and sent to a processor for processing. As in the previous embodiment, the analyte sensor 1200 includes a base 222, lid 1224, and spacers 1227A, 1227B forming the fluid-receiving channel 1225. However, other configurations can be used. The chemically-active region 1234 is provided at any suitable location in the fluid-receiving channel 1225 accessible by the biological fluid sample and the optical read head 1337. As in the previous embodiment, one or more retention tabs 226A, 226B of an attachment member 226 form one or more grasping recesses 229A, 229B that are adapted to be engaged by grasping tabs 336A, 336B of a grasping member 336 formed at the end of the pylon 1310 of an analyte meter (not shown). Accordingly, a single analyte sensor 1200 is grasped by the grasping member 336 and secured to the pylon 1310 such that it can be used for analyte testing.

FIG. 14 illustrates an embodiment of analyte sensor dispenser apparatus 1400. The analyte sensor dispenser apparatus 1400 includes a dispenser body 1405 having a recess 1410 formed therein and extending in the dispenser body 1405, and an opening 1415 on one end thereof. A plurality of analyte sensors (e.g., analyte sensors 200), as are described herein, are provided in a stacked configuration within the recess 1410. Each analyte sensor 200 includes an attachment member (e.g., 226) having one or more retention tabs (e.g., 226A, 226B disposed towards the opening 1415 and adapted to be grasped by grasping tabs 336A, 336B on a pylon 110 of an analyte meter 100 (FIG. 3A-3B). The analyte sensor dispenser apparatus 1400 in the depicted embodiment includes wall perturbations 1418 that alternate between dimensions wider than the length (L) of the analyte sensor (e.g., 200) and narrower than the length (L) of the analyte sensor, such that a slight interference fit is present. In this way, the analyte sensors (e.g., 200) are retained in the recess 1410 regardless of the orientation of the analyte sensor dispenser apparatus 1400, i.e., they will not fall out. Other sensor configurations can likewise be stacked in like dispenser apparatus.

As shown in FIG. 14, the dispenser body 1405 includes an outer portion 1405A that can be made of a moldable plastic, for example, such as a plastic having low permeability for water vapor. The inner portion 1405B can be an insert made of a flexible material (e.g., a flexible rubber, silicone, urethane material, foam, polypropylene, polyethylene or the like) having the perturbations 1418 formed on the walls thereof. The inner portion 1405B can be adhered in the outer portion 1405A by co-molding, by a suitable adhesive, or mechanically fastened therein. Other materials can be used. moreover, the inner and outer portions 1405A, 1405B may be molded from one material.

Figure 15:
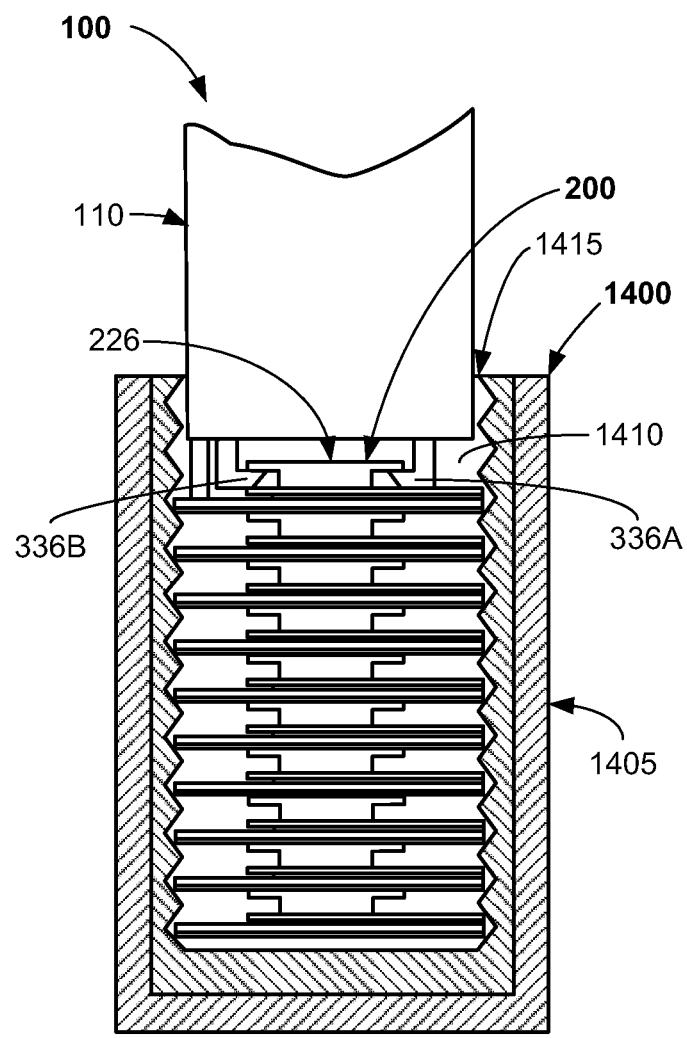
FIG. 15 is a partial cross-sectioned side view of an example embodiment of a pylon of an analyte meter extracting an analyte sensor from an analyte sensor dispenser apparatus.
Figure 16:
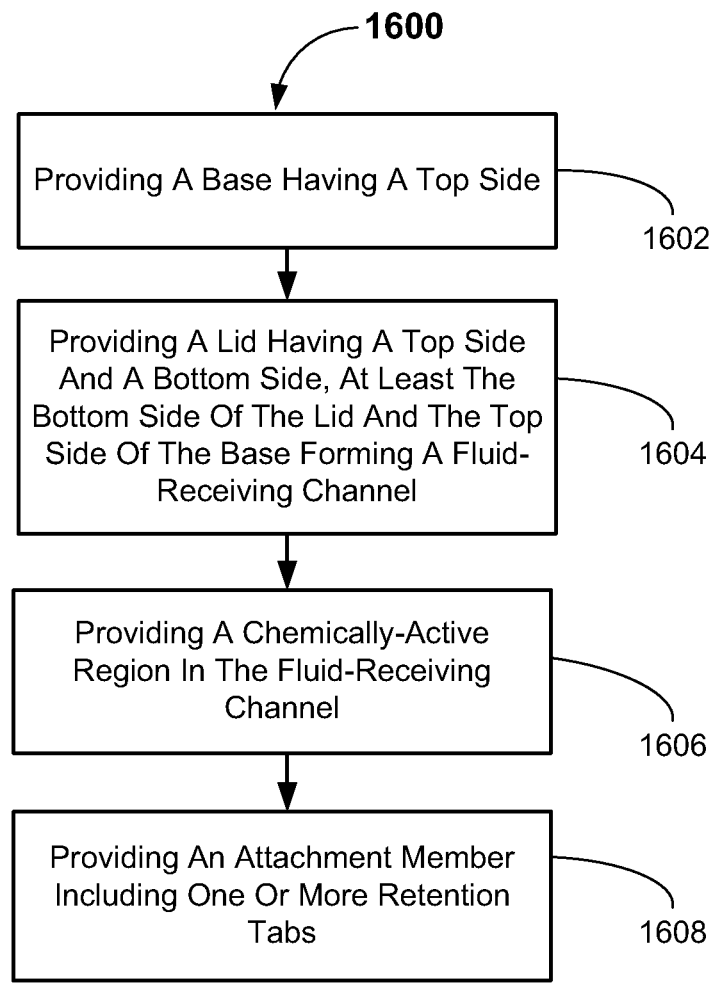
FIG. 16 is a flowchart illustrating a method of manufacturing an analyte sensor.

As shown in FIG. 15, to remove a single analyte sensor (e.g., analyte sensor 200) from the analyte sensor dispenser apparatus 1400, the cap 1405C is removed from the body 1405, and the pylon 110 of the analyte meter 100 (only a portion shown) is inserted into the recess 1410 through the opening 1415. The body 1405 of the analyte sensor dispenser apparatus 1400 is grasped by the user and pushed onto the pylon 110 with a small force to cause the grasping tabs 336A, 336B to move outwardly such that they fall over the one or more retention tabs 226A, 226B and engage the attachment member 226 on a top side of the first analyte sensor 200. To avoid wasting sensors, it is important that only one analyte sensor 200 at a time be allowed to be withdrawn from the analyte sensor dispenser apparatus 1400. The grasping tabs 336A, 336B are able to move outwardly (e.g., laterally) and over the retention tabs 226A, 226B because a distance between the outer edges of the grasping tabs 336A, 336B in the outward position is slightly less than the dispenser opening. Because the base-spacer-lid laminate has a width larger than the retention tabs 226A, 226B, there is no room for the grasping tabs 336A, 336B to bypass the first (uppermost) sensor 200 and accidentally pick up additional sensors. In some embodiments, a space between a top of the grasping tabs 336A, 336B (that engage the one or more retention tabs 226A, 226B) and a lower face of the cam 449 (FIG. 4) is slightly larger than the height of the retention tabs 226A, 226B of the attachment member 226 but smaller than an overall thickness of the laminated base, spacer, and lid of the analyte sensor 200.

As will be understood, a plurality of the analyte sensors (e.g., 200) as described herein can be provided in a stacked configuration within the recess 1410. For example, five or more, 10 or more, or even 15 or more analyte sensors 200 are loaded into the recess 1410 and are engaged, as needed, by inserting the pylon (e.g., 110) into the recess 1410 and engaging the single analyte sensor (e.g., 200) that is closest to the opening 1415. As herein described, each analyte sensor (e.g., 200) of the electrochemical type include electrical contact pads 228B, 230B that are engaged by electrical connectors 335A, 335B of the analyte meter 100 upon engagement between the grasping tabs 336A, 336B and the one or more grasping recesses 229A, 229B. Optionally, in a color change embodiment, as shown in FIG. 12A-13, the read head 1337 is brought into close proximity to the sensor 1200 to read any color change due to exposure to the biological fluid sample.

Methods for manufacturing embodiments of the analyte sensors 1600 of the invention will now be described with reference to FIG. 16, and FIGS. 17A-17L. Methods of manufacturing the analyte sensors 1600 include, in block 1602, providing a base (e.g., 222) having a top side (e.g., 222A). The top side (e.g., 222A), in an electrochemical embodiment, includes an electrical circuit pattern (e.g., 231) formed thereon. In block 1604, a lid (e.g., 224) is provided having a top side (e.g., 224A) and a bottom side (e.g., 224B), at least the bottom side (e.g., 224B) of the lid (e.g., 224) and the top side (e.g., 222A) of the base (e.g., 222) forming a fluid-receiving channel (e.g., 225). In block 1606, a chemically active region (e.g., 234 or 1234) is provided in the fluid-receiving channel (e.g., 225 or 1225). For example, the chemically active region (e.g., 234) is applied to the electrical circuit pattern in an electrochemical embodiment, and the chemically active region (e.g., 1234) is applied to the top side (e.g., 222A) of the base (e.g., 222) in an optical analyte sensor embodiment. Of course, in the optical analyte sensor embodiment, the chemically active region (e.g., 1234) can be applied to any location where the read head 1337 and biological fluid can access it, such as on an underside of the lid 1224.

In block 1608, an attachment member (e.g., 226) is provided including one or more retention tabs (e.g., 226A, 226B). For example, in the depicted embodiments, the one or more retention tabs 226A, 226B can be provided on a top side 224A of the lid 224 (See FIG. 9A), or on a top side 224A of the base 222 (See FIG. 9B). Other top side attachment locations can be employed.

Figure 17A:
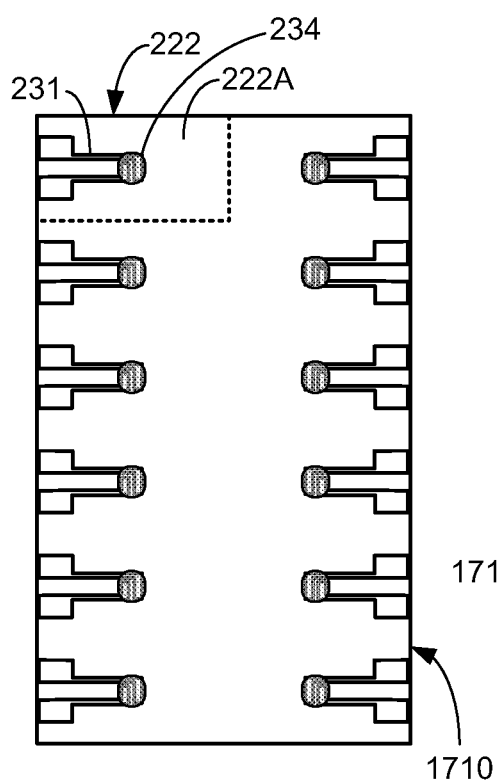
FIGS. 17A-17L illustrate various top plan and side plan views during various stages in a manufacturing method producing analyte sensors.
Figure 17C:
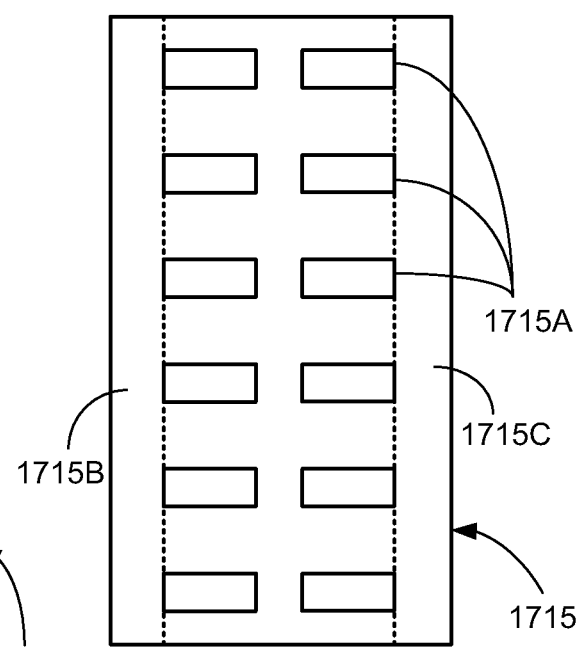
Figure 17B:
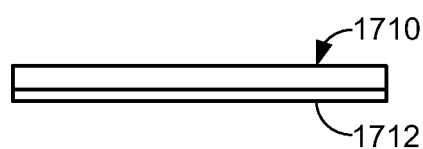

A manufacturing method example will now be described with reference to FIGS. 17A-17L. As shown in FIG. 17A-17B, the base 222 is formed as part of a sheet of base material 1710, and can have an optional hydrophobic layer 1712 on the bottom side thereof. Electrical circuit patterns 231 for multiple analyte sensors 200 are provided on the sheet of base material 1710. The electrical patterns 231 include the electrodes 228, 230, electrical conductors 228A, 230A, and electrical contact pads 228B, 230B for a plurality of analyte sensors 200, as previously described. The electrodes 228, 230, conductors 228A, 230A, and electrical contact pads 228B, 230B can be made of any suitable electrically-conductive material and can be formed by any suitable method as discussed above. For example, in some embodiments, the electrodes 228, 230, conductors 228A, 230A, and electrical contact pads 228B, 230B can be formed with a conductive ink using a screen printing, laser printing, or inkjet printing process, subdivision of a continuous metal layer, or plating, for example. Optionally, the electrodes 228, 230, conductors 228A, 230A, and electrical contact pads 228B, 230B can be formed by adhering a suitably-patterned thin conductive film to the sheet of base material 1710. The electrodes 228, 230, conductors 228A, 230A, and electrical contact pads 228B, 230B can be integrally formed, or formed as two or more individual interconnected components. They can be manufactured from the same or different materials.

In the depicted embodiment, a two column by six row (2×6) pattern is shown. The 2×6 pattern will produce 12 analyte sensors 200. However, it should be recognized that other patterns can be used, such as 2×5, 2×8, 2×10, 2×12, etc. Other patterns can be used as well. A chemically-active region 234 is applied on the top side thereof over at least a portion of each electrical pattern 231 and the gap 232 thereof. The chemically-active region 234 is provided in the fluid-receiving channel described herein. Of course, the electrical pattern 231 would not be applied in manufacturing the color change analyte sensor embodiment.

Figure 17D:
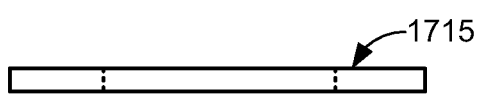

Spacers 227A, 227B (FIG. 2C) are laminated to the base 222. The spacers 227A, 227B are formed as part of a spacer sheet 1715 having many spacers for multiple analyte sensors 200 formed thereon, as shown in FIG. 17C-17D. The spacers (e.g., 227A, 227B) for each analyte sensor 200 can be formed by laser cutting the spacer sheet 1715 through to form through holes 1715A in certain locations and to form at least part of the geometry of the fluid-receiving channel 225 (FIG. 2C). Furthermore, the spacer sheet 1715 can be partially cut (e.g., a kiss cut) along the dotted lines shown in FIG. 17C to form removable wings 1715B, 1715C that are removed later in the manufacturing method.

Figure 17E:
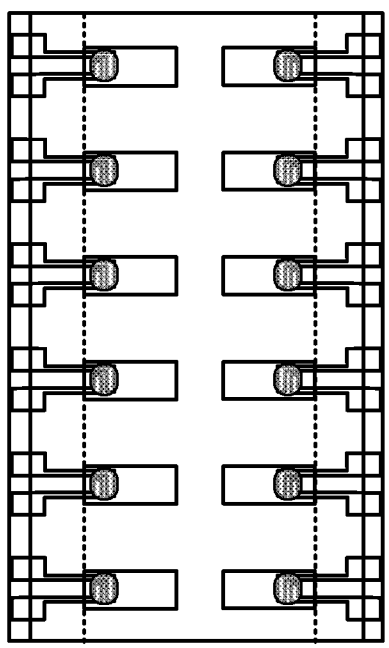
Figure 17G:
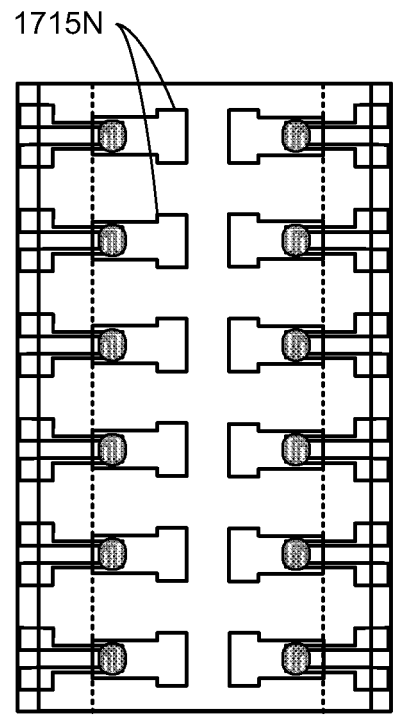
Figure 17F:
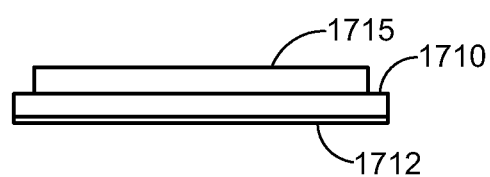

As shown in FIGS. 17E and 17F, the spacer sheet 1715 is laminated to the top side of the sheet of base material 1710 having the numerous electrical circuit patterns formed on the top side. The chemically active regions 234 are applied to each of the electrical circuit patterns before lamination. After lamination, the through holes 1715A in combination with the sheet of base material 1710 form three sides of the fluid-receiving channel 225. The spacer sheet 1715 can be slightly narrower than the sheet of base material 1710. Lamination can be via adhesive, such as a pressure sensitive adhesive, for example, or other known lamination methods. As shown in FIG. 17G, additional nose cuts 1715N can be made through base material 1710 and spacer sheet 1715 that will form the opening of the fluid-receiving channel 225.

Figure 17H:
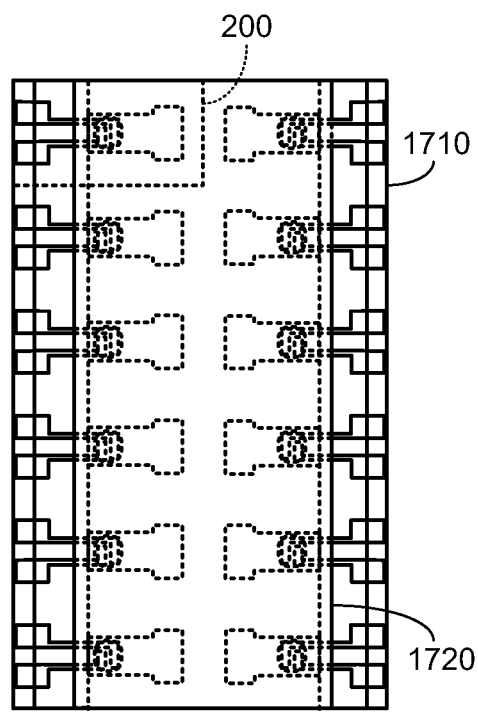
Figure 17I:
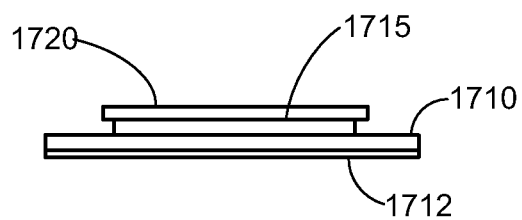

As shown in FIGS. 17H and 17I, a lid sheet 1720 with hydrophilic coating on the underside is laminated to the assembly of the sheet of base material 1710 and spacer sheet 1715, such as with a pressure-sensitive adhesive or the like after removing the wings 1715B, 1715C. The width of the lid sheet 1720 can be wider than the spacer sheet 1715 (with wings removed) to form the overlapping portion of the vent 233 for the analyte sensor 200 (dotted outline of a size of a single sensor 200 shown). After lamination, the hydrophilic surface of the lid sheet 1720 forms the top of the fluid-receiving channel 225.

Figure 17J:
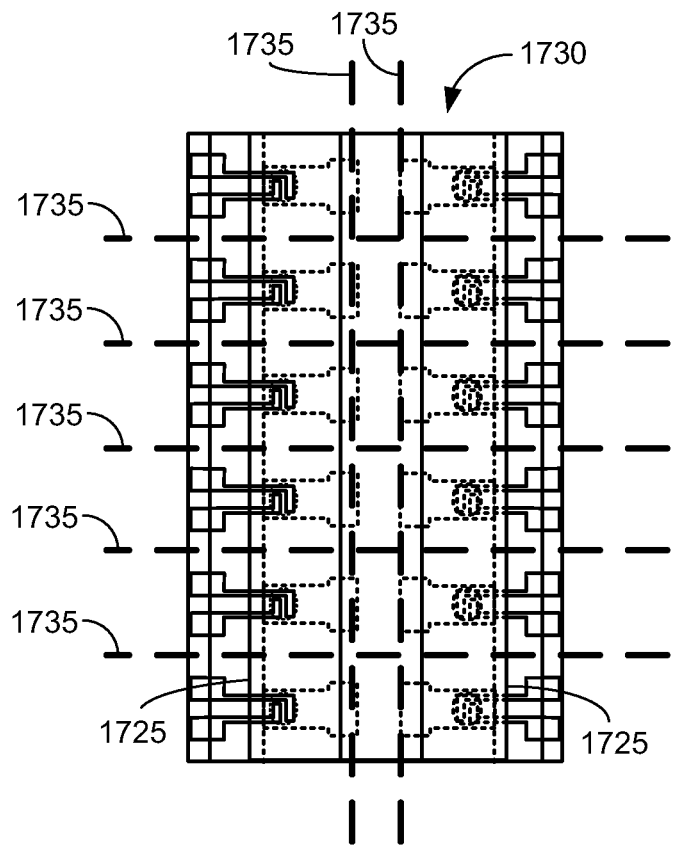
Figure 17K:
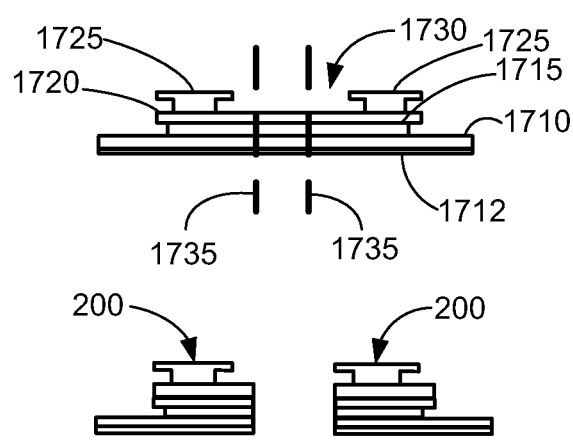
Figure 17L:
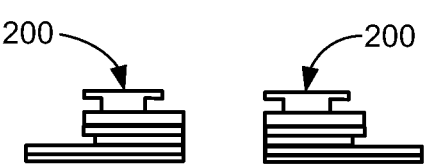

In FIGS. 17J-17K, attachment member strips 1725 are laminated to the top of the lid sheet 1720 to complete the assembly 1730 using pressure-sensitive adhesive, or the like. The assembly 1730 is then cut along dotted cut lines 1735, such as by a die or a laser to form the individual analyte sensors 200 as shown in FIG. 17L. The optical analyte sensor embodiment described herein is manufactured in the same manner, except that the electrode pattern 231 is eliminated, and a chemically-active region 1234 having color change properties is applied. Such chemically active region 1234 exhibiting color change properties are known. In appropriate instances, two or more of the various laminated components described above can be provided as an integral molded component, thereby reducing lamination steps.

The foregoing description discloses only example embodiments of analyte sensors, apparatus, and systems including the same, and methods of manufacturing the analyte sensors of the invention. Modifications of the above-disclosed analyte sensors, apparatus, and systems incorporating them, and methods for manufacturing them, which fall within the scope of the invention, will be readily apparent to those of ordinary skill in the art.

Accordingly, while the present invention has been disclosed in connection with example embodiments thereof, it should be understood that other embodiments may fall within the spirit and scope of the invention, as defined by the following claims.

The invention claimed is:

1. An analyte sensor, comprising:
   a base including a top side and bottom side;
   a lid positioned proximate to the base on the top side;
   an attachment member positioned proximate to the top side, the attachment member configured to attach and secure the analyte sensor to an analyte meter, the attachment member including a tab spacer and one or more retention tabs that form at least a first grasping recess between the tab spacer and the one or more retention tabs adapted to receive a grasping tab of the analyte meter;
   a fluid-receiving channel having an opening adapted to receive a biological fluid sample; and
   a chemically-active region provided in the fluid-receiving channel.

2. The analyte sensor of claim 1, comprising electrical conductors in electrical contact with the chemically-active region.

3. The analyte sensor of claim 1, wherein the lid comprises the attachment member.

4. The analyte sensor of claim 1, wherein the attachment member is attached to a top side of the lid and the retention tabs extend along the top side.

5. The analyte sensor of claim 1, wherein the attachment member includes a first retention tab extending in a first direction and a second retention tab extending in a second direction opposite the first direction.

6. The analyte sensor of claim 5, comprising a hydrophobic layer on the bottom side of the base and a hydrophilic layer on a bottom side of the lid.

7. The analyte sensor of claim 1, wherein the one or more retention tabs form a first grasping recess and a second grasping recess adapted to receive grasping tabs of an analyte meter.

8. The analyte sensor of claim 7, wherein the first grasping recess is formed between the lid, the tab spacer, and a first retention tab the second grasping recess is formed between the lid, the tab spacer and a second retention tab of the attachment member.

9. The analyte sensor of claim 1, further comprising electrical contact pads formed on the top side of the base.

10. The analyte sensor of claim 1 further comprising a first spacer and a second spacer provided on either side of the fluid-receiving channel.

11. The analyte sensor of claim 10 further comprising a vent formed by surfaces of the lid, the first spacer and second spacer, and the base.

12. The analyte sensor of claim 11 further comprising at least one electrical conductor extending through the vent.

13. The analyte sensor of claim 1 further comprising a vent and at least one electrical conductor extending through the vent.

14. A method of manufacturing an analyte sensor, comprising:
   providing a base having a top side;
   providing a lid having a top side and a bottom side, at least the bottom side of the lid and the top side of the base forming a fluid-receiving channel;
   providing a chemically-active region in the fluid-receiving channel; and
   providing an attachment member configured to attach and secure the analyte sensor to an analyte meter, the attachment member including a tab spacer and one or more retention tabs that form at least a first grasping recess between the tab spacer and the one or more retention tabs adapted to receive a grasping tab of the analyte meter.

* * * * *

UNITED STATES PATENT AND TRADEMARK OFFICE
CERTIFICATE OF CORRECTION

| | | |
|---|---|---|
| PATENT NO. | : 9,194,837 B2 | Page 1 of 1 |
| APPLICATION NO. | : 13/589377 | |
| DATED | : November 24, 2015 | |
| INVENTOR(S) | : Steven C. Charlton | |

It is certified that error appears in the above-identified patent and that said Letters Patent is hereby corrected as shown below:

IN THE SPECIFICATION

In Column 1, Line 29, delete "keytones," and insert -- ketones, --, therefor.

In Column 4, Line 63, delete "lid 222 or base 224." and insert -- lid 224 or base 222. --, therefor.

In Column 8, Line 48, delete "Pyrolloquinoline quinine" and insert -- Pyrroloquinoline quinone --, therefor.

In Column 11, Line 5, delete "used." and insert -- used, --, therefor.

IN THE CLAIMS

In Column 14, Lines 27-28, in Claim 8, delete "tab the second grasping recess is formed between the lid, the tab spacer" and insert -- tab, wherein the second grasping recess is formed between the lid, the tab spacer, --, therefor.

Signed and Sealed this
Fifteenth Day of March, 2016

Michelle K. Lee
*Director of the United States Patent and Trademark Office*